United States Patent [19]

Gardner

[11] 4,334,853
[45] Jun. 15, 1982

[54] METHOD OF BURNING INCENSE

[75] Inventor: Samuel M. Gardner, Sparta, N.J.

[73] Assignee: Genieco, Inc., Chicago, Ill.

[21] Appl. No.: 125,470

[22] Filed: Feb. 28, 1980

[51] Int. Cl.³ .............................................. F23Q 2/32
[52] U.S. Cl. ....................................... 431/2; 431/126; 431/295; 422/126
[58] Field of Search ................... 431/2, 125, 126, 288, 431/295; 422/126

[56] References Cited

U.S. PATENT DOCUMENTS

| | | | |
|---|---|---|---|
| 2,621,503 | 12/1952 | Schaefer | 431/295 |
| 3,388,960 | 6/1968 | Cangialosi | 431/126 X |
| 3,706,523 | 12/1972 | Kumm | 431/288 X |
| 3,826,606 | 7/1974 | Hicks | 431/295 |
| 4,099,916 | 7/1978 | Gardner et al. | 422/126 |

FOREIGN PATENT DOCUMENTS 337600  11/1955  Switzerland ........................ 431/125

*Primary Examiner*—Edward G. Favors
*Attorney, Agent, or Firm*—Dithmar, Stotland, Stratman & Levy

[57] ABSTRACT

A plurality of incense beads including beads of different fragrances are threaded in a stack on a carrier rod and a bead at one end of the stack is ignited.

10 Claims, 2 Drawing Figures

METHOD OF BURNING INCENSE

BACKGROUND OF THE INVENTION

The present invention relates to a method for burning incense, and particularly beaded incense. In U.S. Pat. No. 4,099,916 there is disclosed a beaded incense product which comprises a plurality of incense beads, each being a solid body with a hole therethrough, and a rod-like holder which is inserted through the holes in a plurality of the beads to form a stack thereof. The advantage of beaded incense products over prior types of incense is that it permits effective control of the length of time that the incense will burn. Thus, the burning time is readily adjusted by varying the number of beads in the stack on the rod. These and other advantages of the beaded incense product are fully set forth in the aforementioned patent.

But with this beaded incense product, as with other types of incense, only one fragrance of incense has been burned at a time. Different fragrances of incense are known in the art, but in other types of incense such as stick incense and block incense, each stick or block comprises only a single fragrance perfume. The use of the beaded incense product, as taught by the aforementioned patent, contemplated beads of a single fragrance being mounted on a carrier rod.

SUMMARY OF THE INVENTION

The present invention relates to an improved method of burning incense, whereby different fragrances of incense may be burned.

It is a general object of this invention to provide a method whereby different fragrances of incense may automatically be sequentially burned without the necessity of relighting by a user.

It is another object of this invention to provide a method of burning different fragrances of incense, whereby the order in which the fragrances are burned may readily be selected by the user and varied at will.

These and other objects of the invention are attained by providing a method of burning incense comprising the steps of providing a stand including a carrier rod, providing a plurality of incense beads each being a solid body with a hole therethrough and at least certain ones of which are respectively perfumed with different fragrances, threading the beads onto the carrier rod in a stack in a predetermined order such that the stack includes beads having different fragrances, then igniting one of the beads at one end of the stack, whereby the beads will burn continuously one after another to emit a plurality of different fragrances.

Further features of the invention pertain to the particular arrangement of the steps of the method whereby the above-outlined and additional operating features thereof are attained.

The invention, both as to its organization and method of operation, together with further objects and advantages thereof, will best be understood by reference to the following specification taken in connection with the accompanying drawings.

DESCRIPTION OF THE PREFERRED EMBODIMENT

Figure 1:
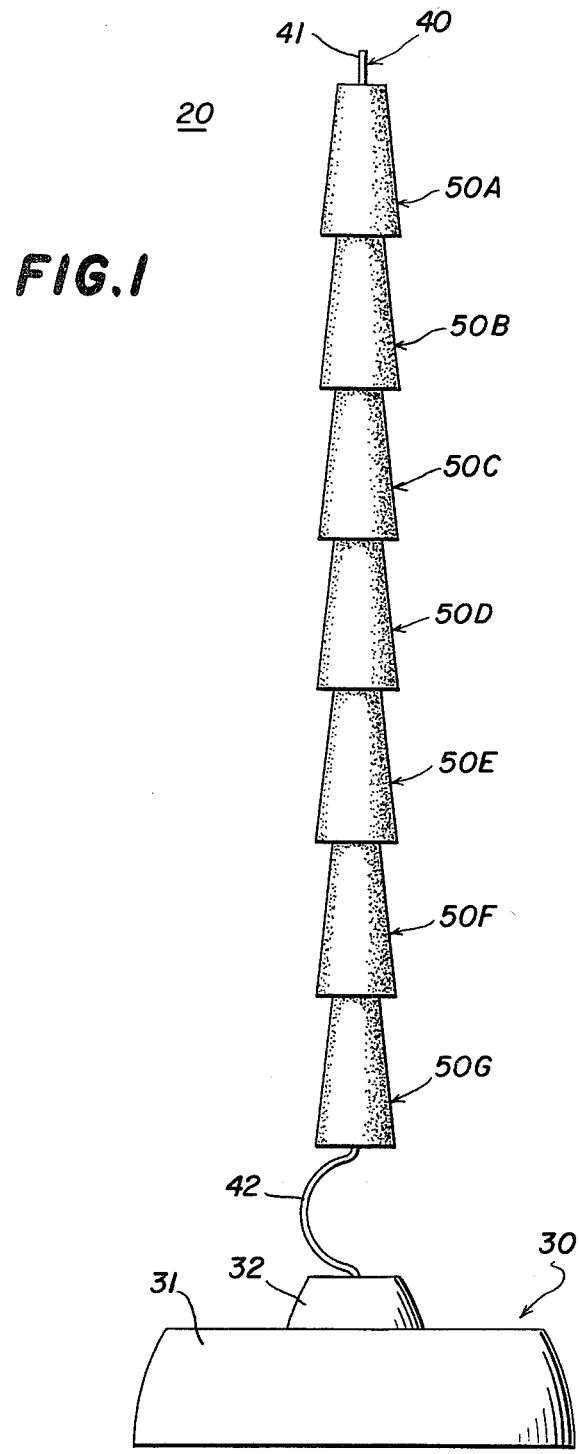
FIG. 1 is a side elevational view of an incense holder having mounted thereon a stack of incense beads of different fragrances.

In FIG. 1 there is illustrated an incense holder, generally designated by the numeral 20, which includes a base 30 supporting thereon a carrier rod 40, formed of metal, wire or the like. More specifically, the base 30 comprises a tray-like bottom portion 31 and a projection 32 extending upwardly above the bottom portion centrally thereof. The carrier rod 40 has an elongated carrier portion 41 and a laterally offset, generally semicircular stop portion 42 adjacent to one end thereof. There is also provided a mounting portion (not shown) which is adapted to be received in a bore in the base projection 32 for mounting the carrier rod 40 in a stable, upright position on the base 30. The details of construction of the incense holder 20 and the manner of operation thereof are disclosed in copending Application (Case 17) Serial No. filed entiled "INCENSE" HOLDER", and assigned to the assignee of the present invention.

Figure 2:
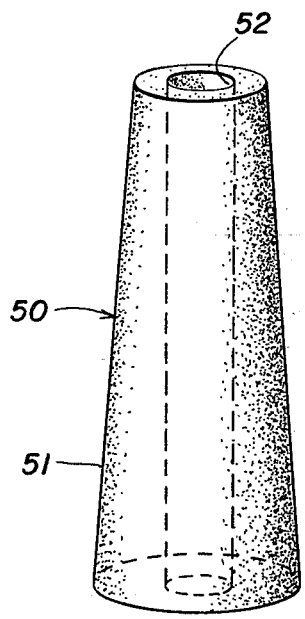
FIG. 2 is an enlarged perspective view of a single one of the incense beads illustrated in FIG. 1.

In use, a plurality of incense beads, generally designated by the numeral 50, is mounted on the carrier rod 40. Referring to FIG. 2, one of the carrier beads is illustrated, the bead 50 having a generally frustoconical outer surface 51 and being provided with an axial bore 52 extending therethrough. Further details of the construction and use of the incense beads are disclosed in the aforementioned U.S. Pat. No. 4,099,916, and it will be appreciated that the incense beads may also be provided in a plurality of other different shapes as more fully set forth in that patent.

But whereas, in the aforementioned patent a plurality of substantially identical beads was mounted on the carrier rod, in the present invention a plurality of similarly-shaped but different fragrance incense beads, respectively designated by the numerals 50A through 50G, is threaded onto the carrier rod 40 by inserting the carrier portion 41 thereof through the bores 52 in the incense beads. Thus, it will be appreciated that when the incense bead at either end of the stack of incense beads on the carrier rod 40 is ignited, the beads will burn one after another, thereby sequentially to emit different fragrances.

As was explained in the aforementioned Patent No. 4,099,916, either the incense bead 50A can be ignited, in which case the beads will burn downwardly through the stack, or the incense bead 50G can be ignited first, in which case the beads will burn upwardly through the stack. By the use of different fragrance beads in the same stack, it will be appreciated that a variety of different patterns of fragrances may be provided.

Thus, for example, an arrangement of beads may be provided for affording a pattern of alternating strong and subtle fragrances. More specifically, the bead 50A could be a relatively strong fragrance such as wisteria, the bead 50B could be a weak or subtle fragrance such as sandalwood, and the bead 50C could have a relatively strong fragrance such as bayberry or another one of the green fragrances such as herbal essence, evergreen or pine. Alternatively, the incense beads could be arranged so as to provide a pattern of fragrances gradually increasing or gradually decreasing in strength. Thus, for example, the bead 50E could have a sandalwood fragrance, the bead 50F could have a wisteria fragrance and the bead 50G could have a fragrance of a flowering shrub such as frangipani. In this manner, it can be seen that a wide variety of different intensities and/or sweetnesses of fragrance can be provided in the same stack of incense beads.

It will be appreciated that the stack of beads on the carrier rod 40 could be arranged so that each bead has a different fragrance from the beads adjacent to it. Alternatively, the beads could be arranged in groups, with each group having a plurality of beads of the same fragrance, but with adjacent groups having different fragrances. Thus, for example, the beads 50A and 50B could have a bayberry fragrance, the beads 50C and 50D could be sandalwood and the beads 50E and 50F could be wisteria. Another alternative is the arrangement of the beads in repeating patterns of fragrances. For example, beads 50A through 50C could be, respectively, sandalwood, wisteria and frangipani and, in like manner, the beads 50D through 50F could be respectively sandalwood, wisteria and frangipani.

In each of these instances once a bead at one end of a stack is ignited, it will burn until it is consumed and then will ignite the next adjacent bead in the stack, whereby the beads will be burned one after another.

Another embodiment of the method of the present invention is the use of more than one incense holder 20 or other similar beaded-incense holder, each incense holder carrying a different stack of incense beads thereon. The several stacks of beads could be arranged in the same pattern or in different patterns and they could have the same or different numbers of beads therein. Also, the several stacks of beads on the several incense holders could be ignited at the same position or at different positions on the stack and they could be ignited at substantially the same time or at different times to provide a wide variety of different effects.

It will be appreciated that the term "different fragrances" as used herein may refer to different types of fragrance, such as wisteria, sandalwood, etc. as explained above, or different intensities of the same type of fragrance, such as weak, regular and strong intensities of wisteria fragrance.

From the foregoing, it can be seen that there has been provided an improved method of burning incense whereby different fragrances of incense may be automatically sequentially burned.

What is claimed is:

1. A method of burning incense comprising the steps of providing a stand including a carrier rod, providing a supply of incense beads each being a solid body with a hole therethrough and perfumed with a fragrance, said supply including a plurality of each of several different fragrances, selecting from the supply a number of beads including beads of different fragrances, removably threading the selected beads onto the carrier rod in a stack in a predetermined order, then igniting one of said beads at one end of the stack, whereby said beads will burn continuously one after another to emit a plurality of different fragrances in the predetermined order.

2. The method of claim 1, wherein said beads are threaded onto said rod in a pattern of alternating intense and subtle fragrances.

3. The method of claim 1, wherein said beads are threaded onto said rod in a pattern of fragrances of gradually varying strength.

4. The method of claim 1, wherein said beads are threaded onto said rod in a pattern of fragrances of gradually varying sweetness.

5. The method of claim 1, wherein said beads are threaded onto said rod in repeating patterns, each pattern comprising a plurality of beads respectively having different fragrances.

6. The method of claim 1, wherein said beads are threaded onto said rod in a pattern such that adjacent beads have different fragrances.

7. The method of claim 1, wherein said beads are threaded onto said rod in a series of groups of beads, each group comprising a plurality of adjacent beads of the same fragrance, and with adjacent groups having different fragrances.

8. The method of claim 1, and further including the steps of providing at least one additional carrier rod, selecting from the supply an additional group of beads for each additional carrier rod with each group including beads of different fragrances, removably threading each group of selected beads in a stack onto an associated carrier rod in a predetermined order, and igniting one of said beads at one end of the stack on each carrier rod.

9. The method of claim 8, wherein said carrier rods respectively carry stacks of beads in different patterns of fragrances.

10. The method of claim 8, wherein said carrier rods respectively carry different number of beads thereon.

* * * * *